(12) United States Patent
Shimizu

(10) Patent No.: US 6,930,214 B2
(45) Date of Patent: Aug. 16, 2005

(54) PROCESS FOR PRODUCING 2,5-BIS (TRIFLUOROMETHYL)NITROBENZENE

(75) Inventor: Tamaki Shimizu, Chiba (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/883,820

(22) Filed: Jul. 6, 2004

(65) Prior Publication Data

US 2004/0242942 A1 Dec. 2, 2004

Related U.S. Application Data

(63) Continuation of application No. PCT/JP03/00660, filed on Jan. 24, 2003.

(30) Foreign Application Priority Data

Jan. 25, 2002 (JP) ........................................ 2002-017229

(51) Int. Cl.[7] ..................... C07C 205/00; C07D 221/18
(52) U.S. Cl. ......................... 568/936; 568/927; 546/77
(58) Field of Search ................................. 568/927, 936; 546/77

(56) References Cited

U.S. PATENT DOCUMENTS 5,565,467 A    10/1996   Batchelor et al.

FOREIGN PATENT DOCUMENTS

GB    2199034 A    *   6/1988

| JP | 9-31030 A | 2/1997 |
|----|-----------|--------|
| JP | 09 031030 A | 2/1997 |

OTHER PUBLICATIONS

S. D. Ross, et al., "Tetrakis–(trifluoromethyl)–biphenyls", J. Am. Chem. Soc., v. 75, pp. 4976–4969 (1953), XP002309512.

K. Yates, et al., "A Critical Test of the Hammett Acidity Function", Can. J. Chem., v. 50, No. 4, pp. 581–583, (1972), XP002967660.

Clark et al, Tetrahedron Lett., vol. 30, p. 2133–2136 (1989).

Ross et al, J. Amer. Chem. Soc., vol. 75, p. 4967–4969 (1953).

Olah et al, J. Org. Chem., vol. 60, p. 7348–7350 (1995).

Yates et al., Canadian Journal of Chemistry, vol. 50, p. 581–583 (1972).

* cited by examiner

*Primary Examiner*—J. Parsa
(74) *Attorney, Agent, or Firm*—Oblon, Spivak, McClelland, Maier & Neustadt, P.C.

(57) ABSTRACT

A process to produce 2,5-bis(trifluoromethyl)nitrobenzene in a high yield from an industrially easily available material by using a substance with which the reaction operation is simple and handling is easy, with a small number of steps under moderate reaction conditions, is provided. 1,4-bis (trifluoromethyl)benzene is nitrated by means of nitric acid in a solvent comprising as an essential component an acid selected from sulfuric acid having a sulfuric acid concentration of from 91 to 100 mass % and fuming sulfuric acid having a sulfur trioxide concentration of higher than 0 mass % and at most 20 mass %.

15 Claims, No Drawings

PROCESS FOR PRODUCING 2,5-BIS(TRIFLUOROMETHYL)NITROBENZENE

TECHNICAL FIELD

The present invention relates to a novel process for producing 2,5-bis(trifluoromethyl)nitrobenzene. 2,5-bis(trifluoromethyl)nitrobenzene is a compound useful as an intermediate of e.g. pharmaceutical preparations and agricultural chemicals and as an intermediate for production of various functional materials.

BACKGROUND ART

As processes for producing 2,5-bis(trifluoromethyl)nitrobenzene, the following processes have been proposed.

(1) A process of nitrating 1,4-bis(trifluoromethyl)benzene by means of 100 mass % nitric acid at from 90 to 105° C. by using 24% fuming sulfuric acid as a solvent to obtain 2,5-bis(trifluoromethyl)nitrobenzene in a yield of 35% (J. Amer. Chem. Soc., 75, 4967 (1953)).

(2) A process of reacting 1,4-bis(trifluoromethyl)benzene with nitric acid for nitration in the presence of $2CF_3SO_3H$—$B(O_3SCF_3)_3$ which is formed by reaction of $BCl_3$ and $CF_3SO_3H$ in a molar ratio of 1:5, to obtain 2,5-bis(trifluoromethyl)nitrobenzene in a yield of 14% (J. Org. Chem., 60, 7348 (1995)).

(3) A process of reacting 4-chloro-3-nitrobenzotrifluoride with $CF_3Cu$ which is formed from $CF_2Br_2$ and copper, in the presence of charcoal for trifluoromethylation to obtain 2,5-bis(trifluoromethyl)nitrobenzene (Tetrahedoron Lett., 30, 2133 (1989)).

However, the above processes have the following drawbacks.

In the process (1), nitric acid is dropwise added to a mixed solution formed by dropwise adding 24% sulfuric acid to 1,4-bis(trifluoromethyl)benzene. In this process, heat is generated when the mixed acid of sulfuric acid and nitric acid is formed, and fuming sulfuric acid having a high concentration is used at a high temperature. Thus, a side reaction such as sulfonation is likely to take place, and the yield tends to be low.

In the process (2), the yield is extremely low. Further, $CF_3SO_3H$ is expensive, such being disadvantageous for industrial production.

In the process (3), $CF_2Br_2$ which is expensive is used. Further, the amount of copper used is 6 times the molar quantity of 1,4-bis(trifluoromethyl)benzene, such being problematic in view of waste water disposal. Further, the process (3) is an uneconomical process, such being disadvantageous for industrial production.

DISCLOSURE OF THE INVENTION

The present invention has been made to overcome the above problems, and it provides a process for producing 2,5-bis(trifluoromethyl)nitrobenzene which is useful as a synthesis intermediate of e.g. pharmaceutical preparations and agricultural chemicals and as an intermediate for production of various functional materials in a high yield, from a starting material which is industrially easily available, by using a substance with which the reaction operation is simple and handling is easy, with a small number of steps under moderate reaction conditions.

Namely, the present invention provides a process for producing 2,5-bis(trifluoromethyl)nitrobenzene, which comprises nitrating 1,4-bis(trifluoromethyl)benzene by means of nitric acid in a solvent comprising as an essential component an acid selected from sulfuric acid having a sulfuric acid concentration of from 91 to 100 mass % and fuming sulfuric acid having a sulfur trioxide concentration of higher than 0 mass % and at most 20 mass %.

BEST MODE FOR CARRYING OUT THE INVENTION 1,4-bis(trifluoromethyl)benzene as the starting material in the present invention may be available as a commercially available product or by a conventional synthesis method. 1,4-bis(trifluoromethyl)benzene having a purity which is conventionally available may be used as it is without e.g. purification.

In the present invention, 1,4-bis(trifluoromethyl)benzene is nitrated in a solvent comprising as an essential component an acid selected from sulfuric acid having a sulfuric acid concentration of from 91 to 100 mass % and fuming sulfuric acid having a sulfur trioxide concentration of higher than 0 mass % and at most 20 mass %.

In a case where sulfuric acid having a sulfuric acid concentration of from 91 to 100 mass % is used, sulfuric acid having a sulfuric acid concentration of at least 96 mass % is preferred, and concentrated sulfuric acid having a sulfuric acid concentration of from 96 to 97 mass %, which is commercially available and easily available, is particularly preferred. By using sulfuric acid having a sulfuric acid concentration of at least 91 mass %, reactivity of the nitration tends to be remarkably high, and an aimed compound can be obtained in a high yield.

In a case where fuming sulfuric acid is used, the concentration of sulfur trioxide in the fuming sulfuric acid is higher than 0 mass % and at most 20 mass %. The concentration of sulfur trioxide is preferably at most 10 mass % in view of e.g. yield. When the concentration of sulfur trioxide in the fuming sulfuric acid is at most 20 mass %, the amount of by-products such as a sulfonate tends to be reduced, and an aimed compound can be obtained in a high yield.

The amount of each of sulfuric acid and fuming sulfuric acid is preferably from 1 to 50 times, particularly preferably from 3 to 30 times, the mass of 1,4-bis(trifluoromethyl)benzene (Formula 1).

The nitration of the present invention is carried out in a solvent comprising as an essential component an acid selected from sulfuric acid having a sulfuric acid concentration of from 91 to 100 mass % and fuming sulfuric acid having a sulfur trioxide concentration of higher than 0 mass % and at most 20 mass % (hereinafter these acids may sometimes be referred to as specific sulfuric acid). The specific sulfuric acid is the above sulfuric acid or the above fuming sulfuric acid in a usual case. The solvent of the present invention may comprise the specific sulfuric acid alone or may contain another solvent in addition to the specific sulfuric acid. As another solvent, an organic solvent is preferred, and a halogen type solvent such as carbon tetrachloride, chloroform, dichloromethane or 1,2-dichloroethane is particularly preferred. The amount of another solvent is preferably from 1 to 50 times the mass of 1,4-bis(trifluoromethyl)benzene. The reaction of the present invention adequately proceeds without using another solvent, and the post-treatment tends to be easy when another solvent is not used, and thus it is preferred to carry out the reaction without using another solvent.

In the present invention, 1,4-bis(trifluoromethyl)benzene is nitrated by means of nitric acid in a solvent comprising the above specific sulfuric acid as an essential component.

As nitric acid, in view of availability and high reactivity, fuming nitric acid having a nitric acid concentration of at least 90 mass % is preferred, and fuming nitric acid having a nitric acid concentration of 94 mass % or 97 mass % is particularly preferred. Further, as nitric acid, nitric acid containing a larger amount of water may be used. When the nitric acid containing a larger amount of water is used, there is such advantages that the nitric acid is easily transported. As the nitric acid containing a larger amount of water, the water content in the nitric acid is preferably at most 35 mass %, particularly preferably higher than 6 mass % and at most 35 mass %, especially preferably higher than 6 mass % and at most 30 mass %. It is one of advantages of the present invention that the reaction of the present invention smoothly proceeds even when nitric acid having a higher water content is used. In a case where nitric acid having a high water content is used as nitric acid, it is preferred to increase the amount of sulfur trioxide or fuming sulfuric acid used.

The amount of nitric acid is preferably from 0.2 to 15 times, particularly preferably from 1 to 10 times, the molar quantity of 1,4-bis.(trifluoromethyl)benzene.

The reaction temperature of the nitration is usually preferably from 50 to 100° C., particularly preferably from 60 to 95° C., in view of a balance between selectivity of the aimed product and the degree of conversion of the starting material.

The reaction time is not particularly limited, preferably, it is suitably determined while analyzing the progress of the reaction usually by e.g. gas chromatography (hereinafter referred to as GC), and it is particularly preferably from about 1 to about 25 hours.

The nitration of the present invention is an exothermic reaction. Further, heat is generated also when the solvent comprising the specific sulfuric acid as an essential component and nitric acid are mixed to form a mixed acid. Thus, it is particularly preferred to carry out the reaction in such a manner that these times when heat is generated are separated, so that operation property when the reaction is controlled tends to be high, and selectivity of the aimed product tends to be high. Specifically, it is preferred to carry out the reaction by the following method in which the method of charge at the time of reaction is contrived. Namely, it is preferred to preliminarily prepare a mixed acid consisting of a solvent comprising the specific sulfuric acid as an essential component and nitric acid, and dropwise add or dividedly add 1,4-bis(trifluoromethyl)benzene in the mixed acid. "Dividedly add" means that the required amount is added dividedly in several times with time difference. Heat can be effectively removed by contriving the method of charge.

Further, in the reaction of the present invention, further nitration after 1,4-bis(trifluoromethyl)benzene is mononitrated to form an aimed compound, can be prevented. Thus, it is sufficient to carry out heat removal operation or heat retaining operation only to control heat generation at the time of nitration. According to the above method of charge, it tends to be easy to control the reaction temperature.

In the above method of charge, the time to dropwise add 1,4-bis(trifluoromethyl)benzene, or the number of addition when it is dividedly added, is not particularly limited and is suitably changed depending upon the reaction scale or the reaction apparatus.

The product after completion of the reaction (hereinafter referred to as crude product) may be used for the intended application as it is, however, in a usual case, it is preferably subjected to post-treatment to obtain one having a higher purity depending upon the purpose. For example, in a case where the crude product is separated into two layers, it is preferred to remove the mixed acid layer and to use the rest as it is for succeeding reaction. Further, the crude product may be subjected to a conventional operation such as extraction to take out 2,5-bis(trifluoromethyl)nitrobenzene, which is further subjected to known purification such as distillation or column chromatography, as the case requires.

2,5-bis(trifluoromethyl)nitrobenzene produced by the process of the present invention is a compound useful as an intermediate of e.g. pharmaceutical preparations and agricultural chemicals and as an intermediate for production of various functional materials.

For example, it can be converted to a compound of the following formula (2) (X in the following formula is a halogen atom or a hydroxyl group) which is promising as a therapeutic agent for prostatic hyperplasia or baldness.

Namely, according to the present invention, a compound of the following formula (2) can be produced by reducing 2,5-bis(trifluoromethyl)nitrobenzene produced by the above process to form 2,5-bis(trifluoromethyl)aniline, which is reacted with a compound of the following formula (1a).

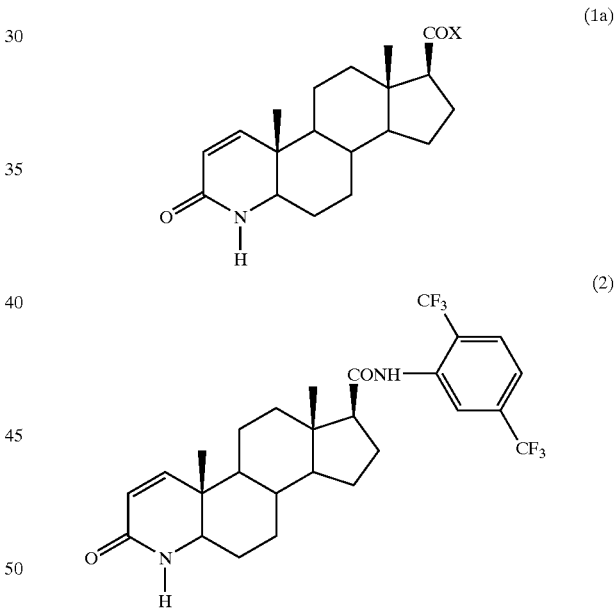

Further, a compound of the formula (2) can be produced by reducing 2,5-bis(trifluoromethyl)nitrobenzene produced by the above process to form 2,5-bis(trifluoromethyl)aniline, reacting the formed 2,5-bis(trifluoromethyl)aniline with a compound of the following formula (1b) to form a compound of the following formula (1c), oxidizing the compound of the formula (1c) to form a compound of the following formula (1d), subjecting the compound of the formula (1d) to ammonia treatment and then to hydrogenation to form a compound of the following formula (1e), and subjecting the compound of the formula (1e) to dehydrogenation:

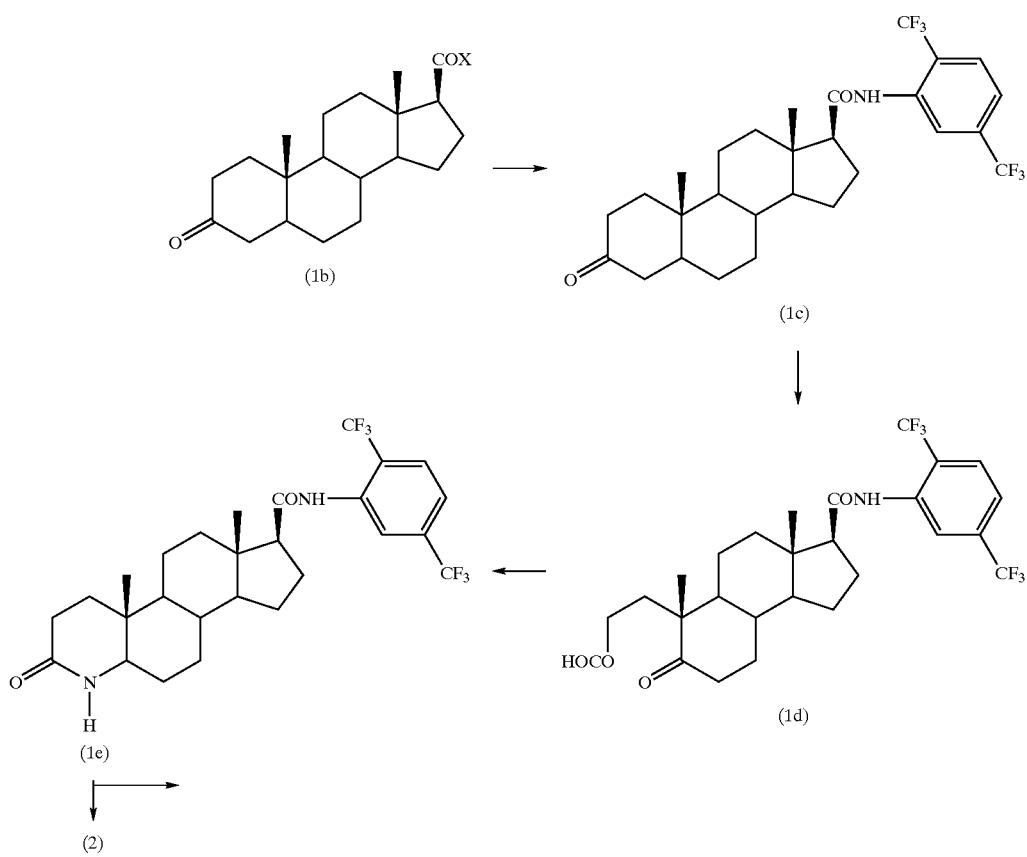

The method of reducing 2,5-bis(trifluoromethyl) nitrobenzene to convert it into 2,5-bis(trifluoromethyl)aniline is a known method (Can. J. Chem., 50(4), 581 (1972). Further, the method for producing the compound of the formula (2) by using 2,5-bis(trifluoromethyl)aniline is also a known method (JP-A-9-502731).

EXAMPLES

Now, the present invention will be described in further detail with reference to Examples. However, it should be understood that the present invention is by no means restricted to such specific Examples. The yield is a value obtained by analyzing a dichloromethane solution before distillation of the product by an internal standard analysis method by means of GC, and it is a yield based on 1,4-bis(trifluoromethyl)benzene.

Example 1

Into a four-necked flask of 3 L, 96 mass % sulfuric acid (1870 ml) was introduced, and 97 mass % fuming sulfuric acid (851 g, 13.1 mol) was dropwise added thereto over a period of 30 minutes under cooling with water. Then, the above mixed acid was heated to 85° C., and 1,4-bis(trifluoromethyl)benzene (400 g, 1.87 mol) was dropwise added thereto over a period of 2 hours. The internal temperature of the flask immediately after the dropwise addition was 95° C. Then, after it was confirmed that the internal temperature of the flask decreased to 85° C., stirring was carried out at 85° C. for 24 hours.

After completion of the reaction, the temperature was recovered to room temperature, and then the mixed acid layer and the organic layer were separated. The mixed acid layer was extracted with dichloromethane. The dichloromethane solution and the above separated organic layer were mixed, and the mixture was washed with a 10 mass % NaOH aqueous solution and then washed with water, dried over anhydrous magnesium sulfate and subjected to filtration. The dichloromethane solution was distilled off under reduced pressure to obtain 2,5-bis(trifluoromethyl) nitrobenzene (281 g, yield 58.0%) having a purity of 99.6% (GC analysis) as a fraction of boiling point 70–73° C./1200 Pa.

As a result of analysis by gas chromatograph mass spectrometry (GC-Mass), $^1$H-NMR and $^{19}$F-NMR, the product was confirmed to be 2,5-bis(trifluoromethyl) nitrobenzene. The yield was 70.3%.

Example 2

The reaction was carried out in the same manner as in Example 1 except that 96 mass % sulfuric acid was changed to fuming sulfuric acid having a sulfur trioxide concentration of 10 mass %, the stirring time was 8 hours, and the temperature at the time of stirring was 80° C., to obtain 2,5-bis(trifluoromethyl)nitrobenzene. The yield was 68.7%.

Example 3

The reaction was carried out in the same manner as in Example 1 except that 96 mass % sulfuric acid was changed to 100 mass % sulfuric acid, the stirring time was 12 hours, and the temperature at the time of stirring was 80° C., to obtain 2,5-bis(trifluoromethyl)nitrobenzene. The yield was 72.7%.

Example 4

The reaction was carried out in the same manner as in Example 1 except that 96 mass % sulfuric acid was changed to fuming sulfuric acid having a sulfur trioxide concentration of 10 mass %, 97 mass % fuming nitric acid was changed to 98 mass % concentrated nitric acid, stirring time was 10 hours, and the temperature at the time of stirring was 80° C., to obtain 2,5-bis(trifluoromethyl)nitrobenzene. The yield was 65.3%.

Example 5 (Reference Example)

The reaction was carried out in the same manner as in Example 1 except that 96 mass % sulfuric acid was changed to 80 mass % sulfuric acid to obtain 2,5-bis(trifluoromethyl) nitrobenzene. The yield was 28.5%.

Example 6 (Reference Example)

The reaction was carried out in the same manner as in Example 1 except that 96 mass % sulfuric acid was changed to 90 mass % sulfuric acid to obtain 2,5-bis(trifluoromethyl) nitrobenzene. The yield was 39.1%.

Example 7 (Comparative Example)

The reaction was carried out in the same manner as in Example 1 except that 96 mass % sulfuric acid was changed to fuming sulfuric acid having a sulfur trioxide concentration of 24 mass % to obtain 2,5-bis(trifluoromethyl) nitrobenzene. The yield was 32.5%.

Example 8

Into an autoclave, 1.05 g of Raney Nickel catalyst (10 wt %) and 100 ml of isopropanol were introduced, and 10.0 g of 2,5-bis(trifluoromethyl)nitrobenzene was added thereto in small amounts. Hydrogen gas was blown until 5 kg/cm$^2$ with stirring, and the temperature was increased to 70° C. Reaction was carried out at from 70 to 90° C. for 8 hours. After the temperature was recovered to room temperature, hydrogen gas was evacuated, and the Raney Nickel was subjected to filtration and washed with isopropanol. The solvent was concentrated to obtain 2,5-bis(trifluoromethyl)aniline (6.42 g, yield 73%, purity by GC 99.4%). As a result of analysis by GC-Mass, $^1$H-NMR and $^{19}$F-NMR, the product was confirmed to be 2,5-bis(trifluoromethyl)aniline.

Example 9

By using 2,5-bis(trifluoromethyl)aniline obtained in the production process of Example 8 and a compound of the above formula (1a) wherein X is a hydroxyl group, reaction was carried out in accordance with a method as disclosed in Example 2 of JP-A-9-502731 to obtain a product. The spectral data of the product corresponded with the data of the compound of the above formula (2) wherein X is a hydroxyl group.

Example 10

By using 2,5-bis(trifluoromethyl)aniline obtained in the production process of Example 8 and a compound of the above formula (1b) wherein X is a hydroxyl group, reaction was carried out in accordance with a method as disclosed in Example 1 of JP-A-9-502731 to obtain a product. The spectral data of the product corresponded with the data of the compound of the above formula (1c) wherein X is a hydroxyl group. Then, the product was reduced in accordance with a method as disclosed in JP-A-9-502731 to obtain a product. The spectral data of the product corresponded with the data of the compound of the above formula (2) wherein X is a hydroxyl group.

INDUSTRIAL APPLICABILITY

According to the process of the present invention, 2,5-bis(trifluoromethyl)nitrobenzene which is useful as a synthesis intermediate of e.g. pharmaceutical preparations and agricultural chemicals and as an intermediate for production of e.g. various functional materials, can be produced in a high yield, from 1,4-bis(trifluoromethyl)benzene which is industrially easily available, by using a solvent comprising as an essential component a specific sulfuric acid with which the reaction operation is simple and handling is easy, and nitric acid, with a small number of steps under moderate reaction conditions.

The entire disclosure of Japanese Patent Application No. 2002-017229 filed on Jan. 25, 2002 including specification, claims and summary is incorporated herein by reference in its entirety.

What is claimed is:

1. A process for producing 2,5-bis(trifluoromethyl) nitrobenzene, which comprises nitrating 1,4-bis (trifluoromethyl)benzene by means of nitric acid in a solvent comprising as an essential component an acid selected from sulfuric acid having a sulfuric acid concentration of from 91 to 100 mass % and fuming sulfuric acid having a sulfur trioxide concentration of higher than 0 mass % and at most 20 mass %.

2. The production process according to claim 1, wherein 1,4-bis(trifluoromethyl)benzene is dropwise added or 1,4-bis(trifluoromethyl)benzene is dividedly added to the mixed solution of the solvent and nitric acid.

3. The production process according to claim 1, wherein the solvent comprises an acid selected from sulfuric acid having a sulfuric acid concentration of from 91 to 100 mass % and fuming sulfuric acid having a sulfur trioxide concentration of higher than 0 mass % and at most 20 mass %.

4. The production process according to claim 1, wherein the solvent comprises sulfuric acid having a sulfuric acid concentration of from 96 to 97 mass %.

5. The production process according to claim 1, wherein the solvent comprises fuming sulfuric acid having a sulfur trioxide concentration of higher than 0 mass % and at most 10 mass %.

6. The production process according to claim 1, wherein the amount of each of sulfuric acid and fuming sulfuric acid is from 1 to 50 times the mass of 1,4-bis(trifluoromethyl) benzene.

7. The production process according to claim 1, wherein nitric acid is fuming nitric acid having a nitric acid concentration of at least 90 mass %.

8. The production process according to claim 1, wherein nitric acid is fuming nitric acid having a nitric acid concentration of 94 mass % or fuming nitric acid having a nitric acid concentration of 97 mass %.

9. The production process according to claim 1, wherein the water content in nitric acid is at most 35 mass %.

10. The production process according to claim 1, wherein the water content in nitric acid is higher than 6 mass % and at most 35 mass %.

11. The production process according to claim 1, wherein the water content in nitric acid is higher than 6 mass % and at most 30 mass %.

12. The production process according to claim 1, wherein the reaction temperature of the nitration is from 50 to 100° C.

13. The production process according to claim 1, wherein the reaction temperature of the nitration is from 60 to 95° C.

14. A process for producing a compound of the following formula (2), which comprises reducing 2,5-bis (trifluoromethyl)nitrobenzene produced by the production process as defined in claim 1 to form 2,5-bis (trifluoromethyl)aniline, and reacting the formed 2,5-bis (trifluoromethyl)aniline with a compound of the following formula (1a):

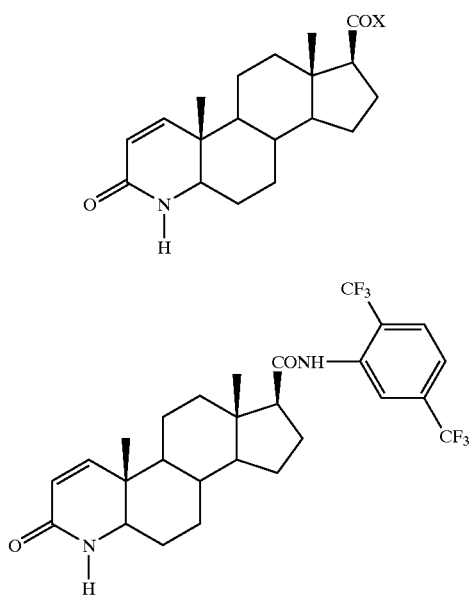
(1a)

(2)

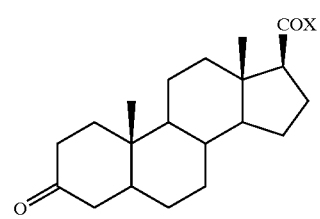

wherein X is a hydroxyl group or a halogen atom.

15. A process for producing a compound of the following formula (2), which comprises reducing 2,5-bis (trifluoromethyl)nitrobenzene produced by the production process as defined in claim 1 to form 2,5-bis (trifluoromethyl)aniline, reacting the formed 2,5-bis (trifluoromethyl)aniline with a compound of the following formula (1b) to form a compound of the following formula (1c), oxidizing the compound of the formula (1c) to form a compound of the following formula (1d), subjecting the compound of the formula (1d) to ammonia treatment and then to hydrogenation to form a compound of the following formula (1e), and subjecting the compound of the formula (1e) to dehydrogenation:

(1b)

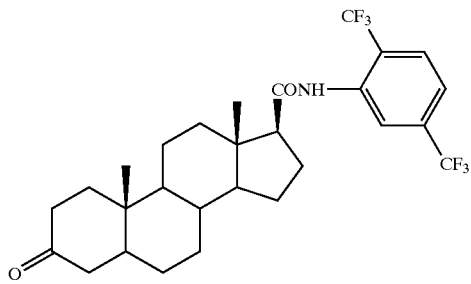
(1c)

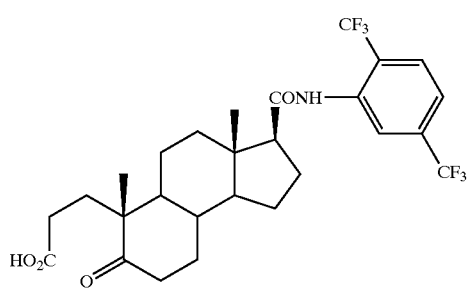
(1d)

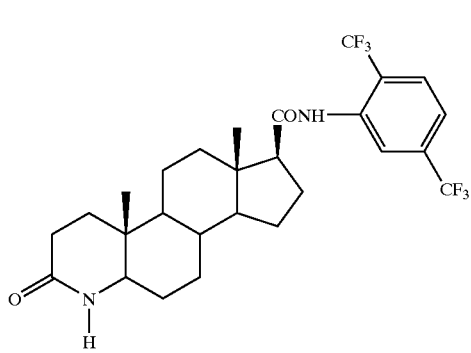
(1e)

(2)

wherein X is a hydroxyl group or a halogen atom.

* * * * *